(12) United States Patent
King et al.

(10) Patent No.: US 9,668,962 B2
(45) Date of Patent: *Jun. 6, 2017

(54) COMPOSITIONS AND RELATED METHODS FOR ORAL WELLNESS

(71) Applicant: NOWSystem, Inc., Kansas City, KS (US)

(72) Inventors: Janice Lou King, Kansas City, KS (US); Dale Leland Winetroub, Kansas City, KS (US)

(73) Assignee: NOWSystem, Inc., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/137,925

(22) Filed: Apr. 25, 2016

(65) Prior Publication Data

US 2016/0235662 A1 Aug. 18, 2016

Related U.S. Application Data

(63) Continuation of application No. 13/683,817, filed on Nov. 21, 2012, now Pat. No. 9,339,453, which is a continuation-in-part of application No. 13/405,177, filed on Feb. 24, 2012, now Pat. No. 8,961,939.

(51) Int. Cl.

| | | |
|---|---|---|
| *A61Q 11/00* | (2006.01) | |
| *A61K 8/22* | (2006.01) | |
| *A61K 36/00* | (2006.01) | |
| *A61K 8/97* | (2017.01) | |
| *A61K 8/34* | (2006.01) | |
| *A61K 8/73* | (2006.01) | |
| *A61K 8/60* | (2006.01) | |
| *A61K 36/534* | (2006.01) | |
| *A61K 36/736* | (2006.01) | |
| *A61K 36/886* | (2006.01) | |
| *A61K 36/899* | (2006.01) | |
| *A61K 47/10* | (2017.01) | |

(52) U.S. Cl.
CPC .............. *A61K 8/97* (2013.01); *A61K 8/345* (2013.01); *A61K 8/60* (2013.01); *A61K 8/73* (2013.01); *A61K 36/534* (2013.01); *A61K 36/736* (2013.01); *A61K 36/886* (2013.01); *A61K 36/899* (2013.01); *A61K 47/10* (2013.01); *A61Q 11/00* (2013.01); *A61K 2800/591* (2013.01); *A61K 2800/5922* (2013.01)

(58) Field of Classification Search
USPC ............... 424/49, 53, 58, 401, 485; 514/901
See application file for complete search history.

(56) References Cited

U.S. PATENT DOCUMENTS

| | | | | |
|---|---|---|---|---|
| 2004/0037790 A1* | 2/2004 | Watanabe | ............... | A61K 8/63 424/58 |
| 2007/0122492 A1* | 5/2007 | Behr | ..................... | A61Q 17/04 424/725 |
| 2007/0166238 A1* | 7/2007 | Duggan | ............... | A61K 9/5073 424/46 |
| 2010/0247563 A1* | 9/2010 | Hines | ...................... | A61K 8/97 424/195.16 |
| 2011/0097284 A1* | 4/2011 | Bottner | .................... | A61K 8/99 424/48 |
| 2013/0280181 A1* | 10/2013 | Nesta | ...................... | A61K 8/27 424/49 |

FOREIGN PATENT DOCUMENTS

WO WO 2011068813 * 6/2011

OTHER PUBLICATIONS

Healing Vibes, Organic Wheat Grass Powder—New Zealand, http://www.healingvibes.com/products/foods/wheatgrass.html, May 2008, pp. 1-3.*
Nowsystem, ELEVA Naturals Products, http://www/hotfrog.com/Companies/Nowsystem/EL%C3%89VA-Naturals-Products-758086, Nov. 25, 2011, p. 1.*
Green Planet Company, PerioPaste—Natural Toothpaste, http://www.greenplanetcompany.net/periopaste.html, May 2009, pp. 1-2.*

* cited by examiner

*Primary Examiner* — Lezah Roberts
(74) *Attorney, Agent, or Firm* — Polsinelli PC

(57) ABSTRACT

The present invention provides for an oral serum made from natural ingredients that advantageously reduces oral bacteria. Further, toothpaste and oral rinse compositions are provided. A method for reducing oral bacteria using the oral serum of the present invention is additionally described herein.

19 Claims, No Drawings

COMPOSITIONS AND RELATED METHODS FOR ORAL WELLNESS

CROSS-REFERENCE TO RELATED APPLICATIONS

This application is a continuation-in-part application of U.S. patent application Ser. No. 13/405,177, which is incorporated by reference herein.

FIELD OF INVENTION

The present application is within the field of compositions and related methods or systems of health and oral care.

BACKGROUND OF THE INVENTION

Poor oral health is thought to contribute to a person's declining general health. For instance, the U.S. Surgeon General has reported findings of possible associations between poor oral health and diabetes, heart and lung diseases, strokes, low birth weight and premature births. Surgeon General's Report on Oral Health, May 2000. Accordingly, there is a need for compositions and related methods or systems of oral health care.

A major focus of correcting poor oral health has heretofore been oral hygiene and compositions and related methods have long been known and used for this purpose. Typically, such compositions are usually applied in some manner to the soft and hard tissues of an oral cavity and suitably contain active ingredients for cleaning and whitening teeth, medicinally treating ailments in the oral cavity soft tissue (e.g., gums), and killing disease or halitosis causing bacteria or fungi occupying the oral cavity. See, e.g., U.S. Pat. No. 0,030,834 (issued Dec. 4, 1860) (col. 2: 1-17 disclosing a fungicidal composition for cleaning and whitening teeth, preventing tooth decay, toothache pain relief, gum treatments, and bad-breath removal); U.S. Pat. No. 0,050,110 (issued Nov. 26, 1865) (col. 1: 9-15 disclosing a scented composition for cleaning teeth and preventing tooth decay); U.S. Pat. No. 0,069,393 (issued Oct. 1, 1867), U.S. Pat. No. 0,085,166 (issued Dec. 22, 1868), U.S. Pat. No. 0,111,821 (issued Feb. 14, 1871), U.S. Pat. No. 0,196,275 (issued Oct. 16, 1877), U.S. Pat. No. 0,284,751 (issued Sep. 11, 1883), U.S. Pat. No. 1,467,455 (issued Sep. 11, 1923), U.S. Pat. No. 1,527,523 (issued Feb. 24, 1925), U.S. Pat. No. 4,407,788 (issued Oct. 4, 1983), U.S. Pat. No. 4,153,680 (issued May 8, 1979), U.S. Pat. No. 4,153,680 (issued Dec. 1, 1981), U.S. Pat. No. 5,939,050 (issued Aug. 17, 1999) (disclosing compositions for cleaning components of the oral cavity); U.S. Pat. No. 0,108,845 (issued Nov. 1, 1870) (col. 1: 1-9 disclosing a composition "for cleansing and preserving teeth, healing diseased gums, tightening loose teeth, preventing toothache, removing canker, and restoring vitiated breath and taste"); U.S. Pat. No. 0,118,813 (Sep. 12, 1871)(col. 1:9-11 disclosing an antiseptic composition for preserving and beautifying teeth); U.S. Pat. No. 0,129,469 (issued Jul. 16, 1872)(col. 2:13-15 disclosing a composition for "cleaning teeth, purifying the mouth, and sweetening the breath"); U.S. Pat. No. 0,137,542 (issued Apr. 8, 1873) and U.S. Pat. No. 0,428,033 (issued May 13, 1890) (disclosing a mouthwash for freshening breath and treating bleeding or swollen gums); U.S. Pat. No. 1,073,725 (Sep. 23, 1913) (col. 1:8-14 disclosing a composition for strengthening the gums, cleansing the teeth and purifying the breath); U.S. Pat. No. 1,523,840 (issued Jan. 20, 1925) (col. 1:12-19 disclosing a composition "which not only cleans and polishes the teeth, but absorbs impurities, massages the gums, stimulating the soft tissues and increasing the blood supply, and finally has a pleasing and appropriate flavor); U.S. Pat. No. 1,527,523 (issued Feb. 24, 1925); U.S. Pat. No. 1,551,638 (issued Sep. 1, 1925) (disclosing a composition for treating oral diseases); U.S. Pat. No. 1,558,160 (issued Oct. 20, 1925) (col. 1:8-12 disclosing a composition that will clean, stimulate and invigorate the soft tissues composing the oral cavity); U.S. Pat. No. 1,916,403 (issued Jul. 4, 1933); U.S. Pat. No. 2,697,060 (issued Dec. 14, 1954) (disclosing a composition for the treatment of inflamed gums (i.e., gingivitis)); U.S. Pat. No. 2,955,985 (issued Oct. 11, 1960) (disclosing a composition for strengthening the gums); and, U.S. Pat. No. 3,124,506 (issued Mar. 10, 1964) (col. 1:17-31 disclosing compositions featuring "tartar removing agent, antienzyme, and sanitizer"); U.S. Pat. No. 3,137,632 (issued Jan. 16, 1964) (disclosing compositions for treating and curing wounds and gum disease); U.S. Pat. No. 5,122,365 (issued Jun. 16, 1992), U.S. Pat. No. 5,171,564 (issued Dec. 15, 1992), U.S. Pat. No. 5,858,332 (issued Jan. 12, 1999) (disclosing teeth whitening); U.S. Pat. No. 3,956,478 (issued May 11, 1976); U.S. Pat. No. 4,242,323 (issued Dec. 30, 1980) (disclosing plaque inhibiting compositions); U.S. Pub. Pat. App. No. US20080031831 (published Feb. 2, 2008) (disclosing an anti-calculus composition comprised of an antiseptic and anti-inflammatory); US20050201953 (published Aug. 15, 2005) (disclosing bacteria killing compositions for freshening breath and disease prevention). However, correcting poor oral health and oral illness requires, among other things and in addition to oral hygiene, the systematic removal of toxic loads provided to the oral cavity, delivery of nutrients to the oral cavity, and rejuvenation of the oral cavity. For this reason, known oral hygiene compositions and related methods fall short of adequately addressing the need for compositions and related methods or systems of oral health care.

Removal of toxic loads is critical in terms of oral health and oral wellness because toxins (e.g., such as Propylene Glycol, Sodium Lauryl Sulfate, Polyethylene, and the like) have been linked to various bodily ailments (e.g., joint pain, skin irritations, hair loss, depression, diarrhea, mouth sores, and cold like symptoms). In an effort to remove toxic loads provided to the oral cavity, known oral hygiene compositions have been comprised of non-toxic ingredients. See e.g., U.S. Pat. No. 0,030,834 (disclosing a composition that does not contain "poisonous ingredients . . . so that it can be used with perfect safety and without danger."). However, merely omitting toxic ingredients from dentifrice compositions does not address the need for active removal of toxic loads from the oral cavity. Others have proposed composing dentifrices of natural ingredients including a fraction containing anti-oxidant rich plant extracts. See U.S. Pat. No. 7,083,779 (issued Aug. 1, 2006). However, even while possessing anti-oxidants, known compositions have failed to provide nutrients to the oral cavity. For these reasons, a need still exists for compositions and related methods or systems of oral health care.

Oral nutrition is also important for oral health and oral wellness. Nutrients have previously been provided to the oral cavity via the use of an oral hygiene composition including a nutrient rich fraction wherein nutrients therefrom are absorbed by the soft-tissue components of the inner oral cavity. See U.S. Pat. No. 1,916,403 (issued Jul. 4, 1933)(col. 1:37-2:56 (disclosing the addition of citrus plant pieces to a dentifrice composition so that Vitamin A, B, and C can be absorbed through the gums while the user is brushing his/her teeth); see also U.S. Pat. No. 6,207,137

(issued Mar. 27, 2001) (disclosing a dentifrice with an active component having Vitamin C in an amount of 10 and 25 weight percent) and U.S. Pat. No. 5,294,434 (issued Mar. 15, 1994) (disclosing use of aloe vera and chlorophyll in an oral hygiene composition to stimulate tissue cell growth). Although absorption of nutrients through the soft-tissues of the oral cavity is suitable for nutrient delivery in terms of oral health care, the known compositions employing such a delivery mechanism can be improved in terms of the types and concentrations of nutrient rich ingredients within a composition and methods or systems of for delivering the composition. More specifically, the recited patents (U.S. Pat. Nos. 1,916,403, 6,207,137 and, 5,294,434) disclose absorption of nutrients from citrus fruit, aloe vera or vitamin powder composing pastes/gels that are contacted to the gums while brushing teeth, yet: other types of ingredients may be more nutrient rich while simultaneously possessing better oral hygiene characteristics; and, other compositions and modes of soft-tissue contact may be more conducive to nutrient absorption. Additionally, the known compositions disclosing nutrient absorption do not feature active removal of toxic loads provided to the oral cavity. For these reason, a need still exists for compositions and related methods or systems of health and oral care.

In addition to the above identified inadequacies of known oral hygiene compositions, known methods and systems for the application of compositions to the oral cavity are also inadequate in terms of treating and preventing poor oral health. Once again, known methods and systems for the application of compositions to the oral cavity focus on promoting oral hygiene or other issues instead of treating poor oral health. See U.S. Pat. Ser. No. U.S. Pat. No. 0,030,834 (disclosing every day application of a oral hygiene cream), U.S. Pat. No. 0,069,393 (disclosing a lozenge for oral hygiene), U.S. Pat. No. 5,098,297 (issued Mar. 24, 1992) (disclosing an apparatus for placing desensitizer on a tooth), U.S. Pat. No. 5,616,187 (issued Mar. 18, 1997) (disclosing an portable apparatus for placing teeth whitener on a tooth), U.S. Pat. No. 4,023,712 (issued May 17, 1977) (disclosing a portable breath spray), and U.S. Pat. No. 7,309,185 (issued Dec. 18, 2007) (disclosing a portable toothbrush with self contained toothpaste); see also U.S. Pub Pat. App. Nos. 20050158252 (published Jul. 21, 2005) (disclosing an oral hygiene solution that is administered in drinking water), 20070292372 (published Dec. 20, 2007) and 20070292367 (published Dec. 20, 2007) (disclosing a method for regular application of oral compositions), and 20090202452 (published Aug. 13, 2009) (disclosing daily and monthly applications of different types of oral hygiene compositions). The known oral hygiene compositions fail to account for harmful bacteria growing in the oral cavity twenty-four hours a day, toxic loads being periodically provided to the oral cavity throughout the day, and multiple daily doses of nutrients being preferable for rebuilding healthy oral cavity cells and immune system support. Also, many of the available compositions and related methods have been expensive and can only be acquired and practiced at a dentist's office. For these reasons, there is a need for compositions and related methods/systems that provide all-day oral health care and that are readily available to the general public.

Known dentifrice compositions and oral medications have not yet been entirely satisfactory for treating poor oral health, particularly in circumstances where oral tissue has become extremely sensitive. For instance, oral diseases or conditions such as dry mouth (Xerostomia) or thrush (candidiasis oral), which are frequently associated with the use of prescription and over-the-counter drugs (There are over 400 prescription and over the counter drugs that cause dry mouth symptoms (e.g., Xerostomia is common due to radiation or chemotherapy treatments)), often result in oral tissue that is too sensitive for topical treatment by effective dentifrice or medicated treatments (extreme cases of thrush sometimes result in oral tissue that is so sensitive that the infected person would rather starve or dehydrate than contact the oral cavity with food or water). Accordingly, a need exists for natural compositions and related methods/systems for treating sensitive oral tissue.

Yet still, known dentifrice compositions and oral medications have not been entirely satisfactory in circumstances where subgingival oral health is poor. For example, periodontal (gum) disease has, in the past, been treated by scaling and root planing (e.g., scraping the disease causing bacteria from between the teeth and gums of the patient) plus application of medications such as chlorhexidine and Arestin® Minocycline HCl (Arestin® is a powder-like antibiotic substance that is deposited between the teeth and gums after scaling and planing). Arestin® has not been entirely satisfactory for treating subgingival oral health because, among other things: use of Arestin®, a tetracycline class drug, may cause permanent discoloration of the teeth and gums, and therefore, should not be used in children or in pregnant or nursing women; hypersensitivity reactions (e.g., anaphaylaxis, angioneurotic edema, urticaria, rash, swelling of the face, pruritus, headache, infection, flu syndrome, and pain have been reported with use of Arestin®); minocycline may cause upset stomach, diarrhea, dizziness, unsteadiness, drowsiness, mouth sores, and vomiting; Arestin® is not a naturally-occurring antibiotic, but is rather synthesized semi-synthetically from natural tetracycline antibiotics and comprised of potentially toxic ingredients; and, as an antibiotic, it does not promote growth and healing of damaged oral tissue. The effects of Chlorhexidine gluconate on periodontitis have not been entirely determined. However, it is thought that Chorhexidine is not entirely satisfactory for treating oral health because: an increase in supragingival calculus has been noted in clinical testing; Chlorhexidine's effectiveness and safety have not been established in children under the age of 18; Chlorhexidine gluconate often causes staining of oral surfaces, including tooth surfaces, restorations, and the dorsum on the tongue; chlorhexidine may cause alterations in taste perception, which in some instances result in permanent taste alteration; chlorhexidine may have the side effects of burning sensations of the oral soft tissues, soreness and dryness of the oral tissues, and desquamative lesions and ulcerations of the gingival mucosa; and, Chlorhexidine has a strong and unpleasant taste. Thus, there remains a need for natural compositions and related methods/systems for treating subgingival oral health conditions in patients of all ages and stages of overall health and wellness.

SUMMARY OF THE INVENTION

It is an object of the present application to disclose non-toxic and nutrient rich compositions and related methods or systems of health and oral care in addition to oral hygiene applications. More specifically, it is an object of the present invention to provide compositions and related systems and methods for treating poor oral health, including the promotion of oral hygiene, reduce or eliminate bacteria in the oral cavity, active toxic load reduction, rejuvenation of the oral cavity, and to provide nutrients to the oral cavity. It is a further object of the present invention to provide compositions that may be applied to the oral cavity in a number of different manners. It is another object of the present application to disclose compositions and methods for all-day oral health care. It is yet still an object of the present invention to provide compositions and related methods that are readily available and inexpensive. It is yet still an object of this disclosure to provide compositions and related methods for controlling mouth infections and bacteria (e.g., periodontal disease) via providing pain reduction, inflammation reduction, odor control (e.g., via killing odor causing bacteria such as sulfur producing anaerobic bacteria), and, promotion of damaged tissue repair. It is yet still another object of the present disclosure to provide compositions and related methods which are safe for children, pregnant and nursing women, the elderly, and special-care individuals.

A first preferable embodiment of this disclosure for implementing the recited objectives may be a non-toxic rinse, gel, toothpaste, or serum composition for topical or subgingival application to the inner components of an oral cavity (e.g., teeth, gums, throat, and/or tongue). The rinse composition may be a mouth rinse or a mouth spray for topical application to the oral cavity. The gel composition may be for topical treatment of the oral cavity or for toothpaste. The serum composition may be used for treating supragingival or subgingival oral conditions. In one embodiment, the rinse composition may comprise: Distilled Water; Organic Whole Leaf wheat grass; Xylitol from Birch Wood; Certified Organic Vegetable Glycerin; Organic Aloe Vera Juice; Carbamide Peroxide; Sweet Almond Oil; Pure Peppermint Oil; and Xanthan Gum. The toothpaste composition may comprise: Organic Whole Leaf wheat grass; Xylitol from Birch Wood; Certified Organic Vegetable Glycerin; Organic Aloe Vera Powder; Sweet Almond Oil; Pure Peppermint Oil; and, Xanthan Gum. For the treatment of sensitive oral tissue or young children (aged between 2 and 12 years), the gel and rinse composition may be made according to gentle care formulations. The serum composition may comprise: Organic Aloe Vera Juice; Xanthan Gum; Organic Whole Leaf wheat grass; Carbamide Peroxide; Sweet Almond Oil; Pure Peppermint Oil; and Certified Organic Vegetable Glycerin. In any composition, nutrients may be delivered to a user via absorption through the soft tissue of the mouth, bacteria may be controlled or killed, oral wounds/conditions may be treated, breath may be freshened, and teeth may be whitened.

The present invention also provides for oral health compositions. Specifically, an oral serum is provided. Preferably, the oral serum is the starting material for several products, including, but not limited to, an oral rinse product, a gel product, and a toothpaste product. Additionally, a method for reducing oral bacteria, a method of removing debris from the oral cavity, and a method of reducing dry mouth is provided. Finally, a method for improved oral wound healing is provided.

The oral serum of the present invention generally comprises a glycerin source, a liquid, an oxidizing agent, a nut extract or oil, aloe vera, cereal grass, a binder and a *mentha* component. In preferred embodiments, the oral serum additionally comprises a preservative.

The oral serum of the present invention advantageously provides a synergistic effect with regard to the reduction of oral bacteria. The oral serum of the present invention is more effective in combination than when each of the ingredients are taken singularly.

Other objectives and desires may become apparent to one of skill in the art after reading the below disclosure.

BRIEF DESCRIPTION OF THE FIGURES

Not applicable.

DETAILED DESCRIPTION OF PREFERRED EMBODIMENTS

In general, the present application discloses non-toxic compositions that are applied to the internal components of the oral cavity for oral health care. The compositions may be a rinse, an oral care gel, a toothpaste, or a supragingival or subgingival serum. The compositions, among other things, suitably kill harmful pathogens and halitosis causing bacteria or fungus, contain antioxidants for removing toxins, strengthen and whiten teeth, moisturize oral tissue, rejuvenate the oral cavity, and deliver nutrients to the oral cavity to rebuild healthy cells and support the immune system. Additionally, the present application discloses methods of making the compositions and methods of using the compositions. Finally, the present application discloses a system for facilitating good oral health and oral wellness.

The serum of the present invention generally comprises a glycerin source, a liquid, an oxidizing agent, a nut extract or oil, aloe vera, cereal grass, a binder and a *mentha* component.

The glycerin source can be any glycerin source appropriate for an oral product and can be synthetic or natural. The glycerin source is preferably selected from, but is not limited to, animal glycerin or vegetable glycerin. In a most preferred embodiment, the glycerin is vegetable glycerin. Preferably, the glycerin is present in an amount between 10 to about 500 grams, more preferably from about 110 to about 400 grams, still more preferably from about 150 grams to about 300 grams, and most preferably about 200 grams. The percentage of the glycerin source in the serum is preferably from about 25% to about 70%, more preferably, from about 35% to about 60%, still more preferably from about 50% to about 60%, and most preferably about 56%.

The liquid is preferably selected from water or plant juice source. In a preferred embodiment, the liquid is either water, aloe vera juice, or a combination thereof. Preferably, the liquid is distilled water. The liquid is present in an amount of from about 40 to about 100 grams, more preferably from about 50 to about 90 grams, still more preferably from about 60 to about 95 grams, more preferably from about 70 to 90 grams, and most preferably about 80 grams. In a preferred embodiment, the liquid is present at about 15 to about 40% of the serum composition, more preferably about 18% to about 35%, more preferably from about 20% to 30%, and most preferably about 22%.

The oxidizing agent is preferably any agent capable of oxidizing a composition. In a preferred embodiment, the oxidizing agent is a peroxide. The peroxide is preferably selected from hydrogen peroxide, carbamide peroxide, and combinations thereof. In a most preferred embodiment, the oxidizing agent is preferably carbamide peroxide. The amount of oxidizing agent present in the serum of the present invention is dependent on the strength of the composition, where more or less will be utilized depending on the strength of the oxidizing agent. Preferably, the oxidizing agent is present in an amount of from about 15 to 40 grams, more preferably from about 20 to 30 grams, and most preferably, about 26 grams. These numbers assume a 22% solution. In an embodiment with a 100% solution of the oxidizing agent, the serum would preferably contain from about 5 to 15 grams, more preferably about 7 grams. Preferably, the oxidizing agent is present in the composition, assuming a 22% solution, from about 2% to about 15%, more preferably from about 5% to about 10%, more preferably from about 6% to about 8%, and most preferably about 7%. In a most preferred embodiment, the oxidizing agent is carbamide peroxide in a 22% solution.

The nut extract or oil can be any oil or extract from a nut, including, but not limited to, walnuts, almonds, pistachio, peanut, macadamia, hazelnut, pine nut, pecans, and combinations thereof. In a preferred embodiment, the extract or oil is from almonds. Most preferably, the nut extract or oil is almond oil. Preferably, the nut extract or oil is present in the serum of the present invention in an amount of from about 1 to about 36 grams, more preferably from about 5 to about to about 30 grams, still more preferably from about 8 to about 25 grams, still more preferably from about 10 to about 20 grams, and most preferably about 18 grams. Preferably, the nut extract or oil is present in from about 1% to about 20%, more preferably, from about 2% to about 18%, still more preferably from about 3% to about 15%, more preferably from about 4% to about 10%, and most preferably, about 5% of the serum of the present invention.

The aloe vera component can be any form of the aloe vera plant that can be formulated into a serum. While not meant to be limiting, aloe vera juice or water, gel, or powder can be used for purposes of the present invention. In a preferred embodiment, aloe vera powder is used. The amount of aloe vera depends on the type of aloe vera used. Aloe vera powder is the most concentrated, while aloe vera gel is less concentrated, and finally aloe vera water is the least concentrated. While any form of aloe vera will work, the amount will need to be adjusted depending on the form used according to methods known in the art. Preferably, the aloe vera component is present in the serum of the present invention in an amount of from about 1 to 16 grams, more preferably from about 2 to 14 grams, still more preferably from about 3 to 12 grams, and most preferably about 8 grams, assuming the aloe vera powder is used. Preferably, the aloe vera component is present from about 0.1% to about 10%, more preferably, from about 0.5% to about 8%, more preferably from about 1% to about 6%, and most preferably about 2% of the serum of the present invention, assuming that aloe vera powder is used. As a non-limiting example, some forms of aloe vera powder are concentrated to form 100×, so 9 parts liquid to 1 part powder would produce aloe vera gel, and 90 parts water to 1 part aloe vera powder would reconstitute the aloe vera powder to aloe vera juice or water strength. Those of skill in the art will be able to make these determinations depending on the form of aloe vera used.

Cereal grass is provided as one of the elements of the present invention. Cereal grass, includes, but is not limited to, maize, rice, wheat, barley, sorghum, millet, oats, triticale, rye, buckwheat, fonio, *quinoa*, and combinations thereof. In a preferred embodiment, wheat grass is utilized. Any form of cereal grass will work for the present invention. Preferred forms include cereal grass extract, juice, powder, and combinations thereof. In a most preferred embodiment, wheat grass powder is utilized. The amount of cereal grass utilized in the serum of the present invention will depend on the form of cereal grass utilized. For example, cereal grass powder is more concentrated than using fresh cereal grass. Those of skill in the art could determine the conversion depending on the form of cereal grass. Preferably, in an embodiment where cereal grass powder is utilized, it is present in the serum in an amount of from about 1 to about 16 grams, more preferably from about 2 to 14 grams, still more preferably from about 3 to 12 grams, and most preferably about 8 grams, assuming that cereal grass powder is used. Preferably, the cereal grass component is present from about 0.1% to about 10%, more preferably, from about 0.5% to about 8%, more preferably from about 1% to about 6%, and most preferably about 2% of the serum of the present invention, assuming that cereal grass powder is used.

The *mentha* component can be from any *mentha* plant and can be in any form suitable for a serum composition. Preferably, the *mentha* component is selected from, but not limited to *mentha aquatica, mentha arvensis*, which includes corn mint, wild mint, Japanese peppermint, field mind, and pudina; *mentha asiatica*, which includes Asian mint; *mentha australis*, which includes Australian mint; *mentha canadensis; mentha cervina*, which includes Hart's Pennyroyal; *mentha citrate*, which includes Bergamot mint; *mentha crispate*, which includes wrinkled-leaf mint; *mentha dahurica*, which includes dahrian thyme; *mentha diemenica*, which includes slender mint; *mentha laxiflora*, which includes forest mint; *mentha longifolia*, which includes *mentha sylvestris* and horse mint; *mentha piperita*, which includes peppermint; *mentha pulegium*, which includes pennyroyal; *mentha requienii*, which includes Corsican mint; *mentha sachalinensis*, which includes garden mint. Forms of the *mentha* include, but are not limited to, extracts, oils, leaves, and combinations thereof. Preferably, the *mentha* is an essential oil. In a preferred embodiment, the *mentha* is *mentha piperita*, and more preferably, peppermint. In a most preferred embodiment, the *mentha* is peppermint oil. Preferably, the *mentha* component is present in an amount of about 1 to about 10 grams, more preferably about 2 to about 8 grams, more preferably, about 3 to 6 grams, and most preferably, about 4 grams. The amount of *mentha* utilized will vary depending on the nature of the form of the *mentha* plant used. The *mentha* is preferably present in the composition at about 0.1% to 5%, more preferably about 0.2% to about 4%, still more preferably from about 0.5% to about 3%, still more preferably from about 0.8% to about 2%, more preferably from about 1% to about 2%, and most preferably about 1.1%. Methods in the art are known for converting the amount of *mentha* component based on the form of the plant utilized.

The binder can be any composition that attaches to a protein envelope of bacteria. The binder includes, but is not limited to, polysaccharides, vegetable gums, natural gums, and combinations thereof. In particular, preferred binders are selected from, but not limited to xanthan gum, arabic gum, locust bean gum, ghatti gum, tragacanth gum, karaya gum, guar gum, locust bean gum, beta-glucan, chicle gum, dammar gum, glucomannan, mastic gum, *psyllium* seed husks, spruce gum, tara gum, gellan gum, and combinations thereof. Preferred binders include, but are not limited to, arabic gum, guar gum, locust bean gum, vegetable gums, and combinations thereof. In a most preferred embodiment, the binder is a gum produced by bacterial fermentation, more preferably the gum is gellan gum or xanthan gum, and most preferably, xanthan gum. Preferably, the binder is present in the composition from 1 to about 15 grams, more preferably about 2 to about 12 grams, more preferably about 4 to about 10 grams, more preferably about 6 to about 9 grams, and most preferably about 8 grams. The binder is preferably present in the composition at about 0.1% to 5%, more preferably about 0.2% to about 4%, still more preferably from about 0.5% to about 3%, still more preferably from about 0.8% to about 2%, more preferably from about 1% to about 2%, and most preferably about 1.7%.

Finally, in some embodiments, a preservative is included in the serum. The preservative can be any preservative suitable for a serum composition. Preferably, the preservative is a natural preservative, more preferably, the preservative is derived from the plant genus *Lamiacede*, more preferably, the species *Rosmariners*. More preferably, the *Rosemariners* plant is either *R. officinalis* or *R. ericocalyx*. In a most preferred embodiment, the preservative is rosemary oil. The preservative is preferably present in an amount of about 1 to about 10 grams, more preferably about 1.1 to about 8 grams, more preferably, about 1.3 to 6 grams, more preferably about 1.5 to about 4 grams, and most preferably, about 2 grams. The preservative component is preferably present in the composition at about 0.1% to 5%, more preferably, about 0.2% to about 3%, more preferably from about 0.4% to about 1% and most preferably, about 0.5% to 0.6%.

In a preferred embodiment, the oral serum of the present invention comprises about 50% to 60% vegetable glycerin, about 20% to 25% distilled water, about 5% to 10% carbamide peroxide (22% solution); 4% to 6% sweet almond oil, about 1% to 3% aloe vera powder, about 1% to 3% wheatgrass powder, about 1% to 2% xanthan gum, about 1% to 2% peppermint oil, and about 0.2% to 1% rosemary oil.

Advantageously, the oral serum of the present invention provides ingredients that have a surprising synergistic effect when in combination. Specifically, the combination of the ingredients in the serum are more effective at preventing bacterial formation and removing bacterial formation from the oral cavity as any of the ingredients are when administered singularly. Preferably, the oral serum reduces at least 2% more bacteria than the ingredients alone, more preferably at least 3% more bacteria than the ingredients alone, more preferably at least 4% more bacteria than the ingredients alone, even more preferably at least 5% more bacteria than the ingredients alone, more preferably at least 6% more bacteria than the ingredients alone, more preferably at least 8% more bacteria than the ingredients alone, more preferably at least 9% more bacteria than the ingredients alone, more preferably at least 10% more bacteria than the ingredients alone, even more preferably at least 15% more bacteria than the ingredients alone, more preferably at least 20% more bacteria than the ingredients alone, more preferably at least 25% more bacteria than the ingredients alone, still more preferably at least 30% more bacteria than the ingredients alone, more preferably at least 40% more bacteria than the ingredients alone, more preferably at least 50% more bacteria than the ingredients alone, more preferably at least 60% more bacteria than the ingredients alone, more preferably at least 75% more bacteria than the ingredients alone, more preferably at least 80% more bacteria than the ingredients alone, more preferably at least 90% more bacteria than the ingredients alone, more preferably at least 100% more bacteria than the ingredients alone. Preferably, the serum decreases the amount of bacteria by at least 2 times the amount of any single ingredient alone, more preferably by at least 3 times the amount of any single ingredient alone, more preferably by at least 4 times the amount of any single ingredient alone, and most preferably by at least 5 times the amount of any single ingredient alone.

A further embodiment of the present invention provides for the serum of the present invention formulated as a toothpaste composition. A method of using the serum of the present invention as a toothpaste composition is also provided, where the steps of the method include administering the serum of the present invention to the teeth and gums using a toothbrush or other oral cleaning tool. The toothpaste formulation of the present invention comprises the serum of the present invention and may optionally additionally comprise xylitol. The xylitol is preferably present in an amount of from about 1 to about 300 grams, more preferably from about 25 to about 250 grams, more preferably from about 50 to about 200 grams, more preferably from about 100 to about 180 grams, even more preferably from about 120 to about 170 grams, and most preferably about 162 grams. Preferably, the xylitol is present in the composition from about 1% to about 60%, more preferably from about 5% to 58%, more preferably from about 15% to about 56%, more preferably from about 20% to about 55%, more preferably from about 35% to about 50%, and most preferably about 46%.

In a preferred embodiment, the toothpaste composition of the present invention, the composition additionally comprises arabic gum. The arabic gum is preferably present in an amount of about 1 to about 16 grams, more preferably from about 2 to about 14 grams, more preferably from about 3 to about 10 grams, more preferably for about 3.5 to about 8 grams, and most preferably about 4 grams.

Preferably, the serum of the present invention, formulated as a toothpaste composition comprises no glycerin or less glycerin in the serum composition as described herein. The toothpaste composition of the present invention preferably has from about 1% to about 30% glycerin, more preferably from about 3% to about 25% glycerin, still more preferably from about 5% to about 20% glycerin, more preferably from about 6% to about 15%, and most preferably about 14%. However, the toothpaste composition of the present invention may contain 0% glycerin.

In a particular embodiment of the toothpaste composition of the present invention, comprises about 40-50% xylitol; about 10-20% vegetable glycerin, about 20-30% water or aloe vera juice; about 2-8% carbamide peroxide (22% composition); about 1% to 5% almond oil; about 0.5% to about 2% aloe vera powder; about 0.5% to about 2% wheatgrass powder; about 0.1% to about 1% xanthan gum; about 0.1% to about 1% peppermint oil; about 0.1% to about 1% rosemary oil; and about 0.5% to about 2% arabic gum.

In a further embodiment of the present invention, a dental rinse is provided. In one embodiment, the dental rinse of the present invention comprises the serum of the present invention having a greater amount of liquid. The liquid is preferably, water, aloe vera juice, or a combination thereof. Preferably, the water or aloe vera juice is present in the dental rinse in an amount of about 50% to about 95%, more preferably from about 55% to about 90%, more preferably from about 60% to about 89%, still more preferably from about 65% to about 88%, more preferably from about 75% to about 87%, and most preferably about 85%, where the percentage can be only water, only aloe vera juice, or a combination of both.

Additionally, the dental rinse of the present invention can be formulated for young children, the elderly, or those with special needs is provided. The dental rinse for young children, the elderly, or those with special needs of the present invention is preferably formulated without the peroxide component. This embodiment is preferably for the elderly or small children who may inadvertently swallow some of the rinse while using the product.

In yet another embodiment, the dental rinse of the present invention is formulated with citrus oil. The citrus oil may be selected from, but is not limited to, lemon oil, orange oil, lime oil, key lime oil, pomelo oil, citron oil, grapefruit oil, mandarin orange oil, trifoliate orange oil, finger lime oil, Australian round lime oil, desert lime oil, kumquat oil, papedas oil, any oil from hybrid varieties of citrus plants, and combinations thereof. Preferably, the citrus oil is from an orange fruit. The citrus oil is preferably present in an amount of from about 0.1% to about 5%, more preferably from about 0.2% to about 3%, still more preferably, from about 0.3% to about 2% and most preferably about 0.4%.

Xylitol may be present in the dental rinse of the present invention, however, it is not required. In an embodiment where xylitol is included, it is preferably present in an amount of from about 0.1% to about 40%, more preferably about 0.5% to about 37%, more preferably from about 1% to about 30%, more preferably from about 4% to about 25%, still more preferably from about 5% to about 20%, still more preferably from about 6% to about 18% and most preferably from about 8% to about 15%.

In a particular embodiment of the present invention, the dental rinse comprises about 10% to about 20% xylitol, about 45% to about 60% distilled water, about 1% to 5% carbamide peroxide (22% solution), about 1% to about 5% sweet almond oil, about 0.1% to 3% aloe vera powder, about 0.1% to 3% wheatgrass powder, about 0.1% to 3% xanthan gum, about 0.1% to 3% peppermint oil, and about 0.1% to 3% rosemary oil.

The present invention also provides a method for reducing bacteria in the oral cavity, where the method comprises the administration of the serum of the present invention to the oral cavity. In a preferred embodiment, oral bacteria is reduced by at least 5%, more preferably by at least 10%, more preferably by at least 15%, still more preferably by at least 20%, more preferably, by at least 25%, still more preferably by at least 30%, more preferably, by at least 35%, more preferably by at least 40%, still more preferably, by at least 45%, still more preferably by at least 50%, more preferably by at least 55%, still more preferably by at least 60%, still more preferably by at least 65%, more preferably by at least 70%, even more preferably by at least 75%, more preferably by at least 80%, more preferably by at least 85%, still more preferably by at least 90%, more preferably by at least 95%, and most preferably 100% of the bacteria is prevented or reduced. The reduction is bacteria is in comparison to an oral cavity which has not been exposed to the serum of the present invention.

Preferably, any type of disease-causing microorganism(s) found in the oral cavity is reduced by the method of the present invention. In a preferred embodiment, the disease-causing microorganisms that are reduced are selected from, but not limited to, bacteria associated with periodontal disease, bacteria associate with bacterial endocarditis, bacteria associated with respiratory disease, and fungal overgrowth associated with oral candidiasis. Preferably, bacteria associated with periodontal disease include, but are not limited to, *Aggregatibacter actinomycetemcomitans* (Aa); *Capnocytophaga* species (*gingavalis, ochracea, sputigena*) (Cs); *Campylobacter rectus* (Cr); *Porphyromanas gingivalis* (Pg); *Eikenella corrodens* (Ec); *Eubacterium nodatum* (En); *Fusobacterium nucleatum/periodonticum* (Fn); *Prevotella intermedia* (Pi); *Peptostreptococcus* (Micromonas) micros (Pm); *Treponema denticola* (Td); *Tannerella forsythia* (Tf); and combinations thereof. Bacteria associated with bacterial endocarditis include, but are not limited to, *S. sanguis, Haemophilus aphrophilus, A. actinomycetemcomitans, E. corrodents, Capnocytophaga* spp., *Fusobacterium nucleatum*, and combinations thereof. Bacteria associated with respiratory disease include, but are not limited to, *Streptococcus pneumoniae, Streptococcus pyogenes, Mycoplasma pneumoniae, Haemophilus influenza, A. actinomycetemcomitans, Actinomyces israelii, Capnocytophaga* spp., *Eikenella corrodens, Prevotella intermedia, Streptococcus constellatus*, and combinations thereof. Fungi associated with oral candidiasis includes, but is not limited to, *candida albicans*. Additionally, *C. albicans* or *S. mutans* are also reduced by the method of the present invention.

In a further embodiment of the present invention, a method of healing oral wounds is provided. The method includes administration of the serum of the present invention to the oral wound. Preferably, the oral wound is lessened in severity or reduced in size as a result of the method of the present invention. The lessening in severity or reduction of the oral wound is in comparison to the wound prior to carrying out the method of the present invention. Preferably, the oral wound is lessened in severity or size of the wound by at least %, more preferably by at least 10%, more preferably by at least 15%, still more preferably by at least 20%, more preferably, by at least 25%, still more preferably by at least 30%, more preferably, by at least 35%, more preferably by at least 40%, still more preferably, by at least 45%, still more preferably by at least 50%, more preferably by at least 55%, still more preferably by at least 60%, still more preferably by at least 65%, more preferably by at least 70%, even more preferably by at least 75%, more preferably by at least 80%, more preferably by at least 85%, still more preferably by at least 90%, more preferably by at least 95%, and most preferably 100%.

Another aspect of the present invention provides for a method of removing debris in the spaces between the free gingival and tooth and from surgical and extraction sites. The debris removed is normally dead tissue, but may also include, but is not limited to calculus deposits and plaque. Preferably, the debris is detached tissue and irritants, such as tenacious calculus deposits and bacterial plaque remaining in the sulcus (space between the tooth and the free gingiva) after subgingival scaling, root planning or debridement. This method is particularly useful, but not limited to, procedures such as root planing and periodontal scaling, routine prophylaxis, subgingival/sulcal lavage, gingival curettage, core retention, extractions, operative procedures and post-operative procedures. Specifically, in a root planning or periodontal scaling, where the gums have started to pull away from the teeth or the roots of the teeth have hard mineral deposits on them, the method of removing debris of the present invention is accomplished by administering the serum of the present invention to the gingival area. The result is that the debris on the teeth, gums, and under the gum line is reduced or lessened. Preferably, the debris is removed, lessened, or reduced by at least %, more preferably by at least 10%, more preferably by at least 15%, still more preferably by at least 20%, more preferably, by at least 25%, still more preferably by at least 30%, more preferably, by at least 35%, more preferably by at least 40%, still more preferably, by at least 45%, still more preferably by at least 50%, more preferably by at least 55%, still more preferably by at least 60%, still more preferably by at least 65%, more preferably by at least 70%, even more preferably by at least 75%, more preferably by at least 80%, more preferably by at least 85%, still more preferably by at least 90%, more preferably by at least 95%, and most preferably 100%.

DEFINITIONS

"Cereal grass," for purposes of the present invention include grass whose starchy grains can be used in food products. Cereal grass includes, but is not limited to, wheat grass, rice grass, rye grass, oat grass, maize, buckwheat grass, and millet. In a preferred embodiment of the present invention, wheat grass is utilized.

"*Mentha*," as used herein, refers to a genus of flowering plants in the family Lamiaceae. Preferred *mentha* include, but are not limited to *mentha aquatica, mentha arvensis*, which includes corn mint, wild mint, Japanese peppermint, field mind, and pudina; *mentha asiatica*, which includes asian mint; *mentha australis*, which includes Australian mint; *mentha canadensis; mentha cervina*, which includes Hart's Pennyroyal; *mentha citrate*, which includes Bergamot mint; *mentha crispate*, which includes wrinkled-leaf mint; *mentha dahurica*, which includes dahrian thyme; *mentha diemenica*, which includes slender mint; *mentha laxiflora*, which includes forest mint; *mentha longifolia*, which includes *mentha sylvestris* and horse mint; *mentha piperita*, which includes peppermint; *mentha pulegium*, which includes pennyroyal; *mentha requienii*, which includes Corsican mint; *mentha sachalinensis*, which includes garden mint; and combinations thereof.

"Reducing bacteria or disease-causing microorganisms" or "lessening bacteria or disease-causing microorganisms" for purposes of the present invention refers to a reduction in the number of bacteria or disease-causing microorganisms in comparison to the bacteria in an oral cavity that has not been exposed to the products or methods of the present invention.

"Disease-causing microorganism(s)" include any microorganism that is capable of causing disease. The disease-causing organisms specifically include, but are not limited to, bacteria associated with periodontal disease, Bacteria associated with bacterial endocarditis, Bacteria associated with respiratory disease and Fungi associated with oral candidiasis. Preferably, bacteria associated with periodontal disease include, but are not limited to, *Aggregatibacter actinomycetemcomitans* (Aa); *Capnocytophaga* species (*gingavalis, ochracea, sputigena*) (Cs); *Campylobacter rectus* (Cr); *Porphyromanas gingivalis* (Pg); *Eikenella corrodens* (Ec); *Eubacterium nodatum* (En); *Fusobacterium nucleatum/periodonticum* (Fn); *Prevotella intermedia* (Pi); *Peptostreptococcus* (Micromonas) *micros* (Pm); *Treponema denticola* (Td); *Tannerella forsythia* (Tf); and combinations thereof. Bacteria associated with bacterial endocarditis include, but are not limited to, *S. sanguis, Haemophilus aphrophilus, A. actinomycetemcomitans, E. corrodents, Capnocytophaga* spp., *Fusobacterium nucleatum*, and combinations thereof. Bacteria associated with respiratory disease include, but are not limited to, *Streptococcus pneumoniae, Streptococcus pyogenes, Mycoplasma pneumoniae, Haemophilus influenza, A. actinomycetemcomitans, Actinomyces israelii, Capnocytophaga* spp., *Eikenella corrodens, Prevotella intermedia, Streptococcus constellatus*, and combinations thereof. Fungi associated with oral candidiasis includes, but is not limited to, *candida albicans*. Additionally, *C. albicans* or *S. mutans* are also included.

EXAMPLES

Example 1

This example illustrates several embodiments of the present invention and methods of making.

A. Compositions

1. Rinse Compositions

The rinse may be comprised of: distilled water; organic whole leaf wheat grass; xylitol from Birch wood; certified organic vegetable glycerin; organic aloe vera juice; carbamide peroxide; sweet almond oil; pure peppermint oil; and xanthan gum. The disclosed composition has been preferable for ordinary oral health care when the component ingredients are featured in the following amounts: 5.98 gallons of distilled water; 2,395.00 grams of Xylitol; 119.70 grams of Peppermint Oil; 981.90 grams of Vegetable Glycerin; 910.10 grams of Aloe Vera Juice; 718.5 grams of Carbamide Peroxide; 311.30 grams of Sweet Almond Oil; 119.70 grams of wheat grass powder; and, 12.90 grams of Xanthan Gum.

The amounts of the component ingredients within the composition may suitably be manipulated to adjust the oral health care properties of the composition. For instance, in another embodiment, the disclosed composition has also been preferable for treatment of sensitive oral tissue or the oral tissue of young children (ages less than twelve years) when the amount of carbamide peroxide is reduced to zero while the 10 remaining component ingredients are featured in the following amounts: 3.12 gallons of distilled water; 1,197.99 grams of xylitol; 47.92 grams of peppermint oil; 491.18 grams of vegetable glycerin; 455.24 grams of aloe vera juice; 155.74 grams of sweet almond oil; 59.90 grams of wheat grass powder; and, 11.98 grams of xanthan gum. For another instance, the tooth whitening properties of the mouth wash may be preferably enhanced when the component ingredients are featured in the following amounts: 12,093.00 grams of distilled water; 315.00 grams of xylitol; 20.00 grams of peppermint oil; 880.00 grams of vegetable glycerin; 130.00 grams of aloe vera juice; 1,500.00 grams of carbamide peroxide; 150.00 grams of Sweet Almond Oil; 20.00 grams of wheat grass powder; and, 12.00 grams of xanthan gum. For another instance, the composition may be more concentrated for professional oral health care by including the component ingredients in the following amounts: 4.73 gallons of distilled water; 2,395.00 grams of xylitol; 119.70 grams of peppermint oil; 981.9 grams of vegetable glycerin; 910.10 grams of aloe vera juice; 718.50 grams of carbamide peroxide; 311.30 grams of sweet almond oil; 119.70 grams of wheat grass powder; and, 12.90 grams of xanthan gum. In yet another embodiment, the disclosed composition has also been preferable for professional treatment of sensitive oral tissue or young children when the amount of carbamide peroxide is reduced to zero while the remaining component ingredients are featured in the following amounts: 2.37 gallons of distilled water; 1,197.99 grams of xylitol; 47.92 grams of peppermint oil; 491.18 grams of vegetable glycerin; 455.24 grams of aloe vera juice; 155.74 grams of sweet almond oil; 59.90 grams of wheat grass powder; and, 11.98 grams of xanthan gum. The above recited preferable amounts of each ingredient are summarized by Table 1.

TABLE 1

Compositions for the mouth rinses

| Ingredient | Amount |
| --- | --- |
| Ordinary Oral Health Care | |
| distilled water | 5.98 gal. |
| xylitol | 2,395.00 gm |
| peppermint oil | 119.70 gm |
| vegetable glycerin | 981.90 gm |
| *Aloe vera* juice | 910.10 gm |
| carbamide peroxide | 718.50 gm |
| sweet almond oil | 311.30 gm |
| wheat grass powder | 119.70 gm |
| xanthan gum | 12.90 gm |
| Sensitive Tissue Ordinary Oral Health Care | |
| distilled water | 3.12 Gal. |
| xylitol | 1,197.99 gm |
| peppermint oil | 47.92 gm |
| vegetable glycerin | 491.18 gm |
| *Aloe vera* juice | 455.24 gm |

TABLE 1-continued

Compositions for the mouth rinses

| Ingredient | Amount |
|---|---|
| sweet almond oil | 155.74 gm |
| wheat grass powder | 59.90 gm |
| xanthan gum | 11.98 gm |
| Teeth whitening | |
| distilled water | 12,093.00 gm |
| xylitol | 315.00 gm |
| peppermint oil | 20.00 gm |
| vegetable glycerin | 880.00 gm |
| *Aloe vera* juice | 130.00 gm |
| carbamide peroxide | 1,500.00 gm |
| sweet almond oil | 500.00 gm |
| wheat grass powder | 20.00 gm |
| xanthan gum | 12.00 gm |
| Professional Oral Health Care | |
| distilled water | 4.73 gal. |
| xylitol | 2,395.00 gm |
| peppermint oil | 119.70 gm |
| vegetable glycerin | 981.90 gm |
| *Aloe vera* juice | 910.10 gm |
| carbamide peroxide | 718.50 gm |
| sweet almond oil | 311.30 gm |
| wheat grass powder | 119.70 gm |
| xanthan gum | 12.90 gm |
| Sensitive Tissue Professional Oral Health Care | |
| distilled water | 2.37 gal. |
| xylitol | 1,197.99 gm |
| peppermint oil | 47.92 gm |
| vegetable glycerin | 491.18 gm |
| *Aloe vera* juice | 455.24 gm |
| sweet almond oil | 155.74 gm |
| wheat grass powder | 59.90 gm |
| xanthan gum | 11.98 gm |

Those of skill in the art will know well the manner by which the above identified ingredients can be obtained or produced. This said: distilled water may be created by condensing steam; organic whole leaf wheat grass powder may be purchased from Pines International (milled to less than 100 mesh by Union Process, Inc.); xylitol from Birch wood may be purchased from Danisco USA, Inc.; pure peppermint oil may be purchased from ASN/Nutritiongeeks.com; carbamide peroxide may be purchased from American Int'l Chemical, Inc.; organic aloe vera juice and powder, certified organic vegetable glycerin, and sweet almond oil may be purchased from Jedwards Int'l Inc.; and xanthan gum may be purchased from The Great American Spice Company, Inc.

A 7.25 gallon batch of the rinse composition for ordinary oral health care may be prepared by: first, mixing 119.70 grams of wheat grass powder with approximately 0.589 gallons of distilled water until the wheat grass powder hydrates thoroughly (approximately 30 minutes); second, slowly mixing 12.90 grams of xanthan gum and approximately 0.897 gallons of distilled water until no clumps of xanthan gum are present (the mixture should preferably be allowed to thicken for one to two hours); third, mixing 718.50 grams of carbamide peroxide, approximately 4.485 gallons of distilled water, and 910.10 grams of aloe vera juice until the carbamide peroxide is thoroughly dissolved; fourth, mixing 2,395.00 grams of xylitol with the resultant mixture from the third step until the xylitol is thoroughly dissolved; fifth, mixing the mixtures of the first, second, and fourth steps together; sixth, mixing 981.90 grams of vegetable glycerin, 311.30 grams of sweet almond oil, and 119.70 grams of peppermint oil; and, seventh, mixing the mixtures of the fifth and sixth steps at high speed until homogenous.

A 3.75 gallon batch of the rinse composition for ordinary oral health care for sensitive tissue or children may be prepared by: first, mixing 59.90 grams of wheat grass powder with approximately 0.312 gallons of distilled water until the wheat grass powder hydrates thoroughly (approximately 30 minutes); second, slowly mixing 11.98 grams of xanthan gum and approximately 0.468 gallons of distilled water until no clumps of xanthan gum are present (the mixture should preferably be allowed to thicken for one to two hours); third, mixing approximately 2.34 gallons of distilled water and 455.24 grams of aloe vera juice; fourth, mixing 1,197.99 grams of xylitol with the resultant mixture from the third step until the xylitol is thoroughly dissolved; fifth, mixing the mixtures of the first, second, and fourth steps together; sixth, mixing 491.18 grams of vegetable glycerin, 155.74 grams of sweet almond oil, and 47.92 grams of peppermint oil; and, seventh, mixing the mixtures of the fifth and sixth steps at high speed until homogenous.

A 15,120.00 gram batch of the rinse composition for teeth whitening may be prepared by: first, mixing 20.00 grams of wheat grass powder with approximately 1,209.30 grams of distilled water until the wheat grass powder hydrates thoroughly (approximately 30 minutes); second, slowly mixing 12.00 grams of xanthan gum and approximately 1,813.95 grams of distilled water until no clumps of xanthan gum are present (the mixture should preferably be allowed to thicken for one to two hours); third, mixing 1,500.00 grams of carbamide peroxide, approximately 9069.75 grams of distilled water, and 130.00 grams of aloe vera juice until the carbamide peroxide is thoroughly dissolved; fourth, mixing 315.00 grams of xylitol with the resultant mixture from the third step until the xylitol is thoroughly dissolved; fifth, mixing the mixtures of the first, second, and fourth steps together; sixth, mixing 880.00 grams of vegetable glycerin, 150.00 grams of sweet almond oil, and 20.00 grams of peppermint oil; and, seventh, mixing the mixtures of the fifth and sixth steps at high speed until homogenous.

A 6.00 gallon batch of the rinse composition for professional oral health care may be prepared by: first, mixing 119.70 grams of wheat grass powder with approximately 0.473 gallons of distilled water until the wheat grass powder hydrates thoroughly (approximately 30 minutes); second, slowly mixing 12.90 grams of xanthan gum and approximately 0.7095 gallons of distilled water until no clumps of xanthan gum are present (the mixture should preferably be allowed to thicken for one to two hours); third, mixing 718.50 grams of carbamide peroxide, approximately 3.5475 gallons of distilled water, and 910.10 grams of aloe vera juice until the carbamide peroxide is thoroughly dissolved; fourth, mixing 2,395.00 grams of xylitol with the resultant mixture from the third step until the xylitol is thoroughly dissolved; fifth, mixing the mixtures of the first, second, and fourth steps together; sixth, mixing 981.90 grams of vegetable glycerin, 311.30 grams of sweet almond oil, and 119.70 grams of peppermint oil; and, seventh, mixing the mixtures of the fifth and sixth steps at high speed until homogenous.

A 3.00 gallon batch of the rinse composition for professional oral health care for sensitive tissue or children may be prepared by: first, mixing 59.90 grams of wheat grass powder with approximately 0.237 gallons of distilled water until the wheat grass powder hydrates thoroughly (approximately 30 minutes); second, slowly mixing 11.98 grams of xanthan gum and approximately 0.3555 gallons of distilled water until no clumps of xanthan gum are present (the mixture should preferably be allowed to thicken for one to two hours); third, mixing approximately 1.7775 gallons of distilled water and 455.24 grams of aloe vera juice; fourth, mixing 1,197.99 grams of xylitol with the resultant mixture from the third step until the xylitol is thoroughly dissolved; fifth, mixing the mixtures of the first, second, and fourth steps together; sixth, mixing 491.18 grams of vegetable glycerin, 155.74 grams of sweet almond oil, and 47.92 grams of peppermint oil; and, seventh, mixing the mixtures of the fifth and sixth steps at high speed until homogenous. Those skilled in the art will appreciate how this formulation(s) may be scaled up or down to accommodate different batch sizes.

2. Gel Compositions

The gel composition may comprise: organic whole leaf wheat grass; xylitol from Birch wood; certified organic vegetable glycerin; organic aloe vera juice; sweet almond oil; pure peppermint oil; and, xanthan gum. The disclosed composition has been most preferable for oral health care when the component ingredients are featured in the following amounts: 4.00 grams of organic whole leaf wheat grass powder; 200.00 grams of xylitol from Birch wood; 200.00 grams of certified organic vegetable glycerin; 200.00 grams of organic aloe vera juice; 50.00 grams of sweet almond oil; 4.00 grams of pure peppermint oil; and, 8.00 grams of xanthan gum. The above preferable compositions are summarized by Table 2.

TABLE 2

Compositions for the oral care gel

| Ingredient | Amount |
| --- | --- |
| wheat grass | 4.00 gm |
| xylitol | 200.00 gm |
| vegetable glycerin | 200.00 gm |
| *Aloe vera* juice | 200.00 gm |
| almond oil | 50.00 gm |
| peppermint oil | 4.00 gm |
| xanthan gum | 8.00 gm |

A 666.00 gram batch of the oral care gel may be prepared by: first, mixing 20.00 grams of aloe vera juice with 4.00 grams of wheat grass powder until the wheat grass powder is thoroughly hydrated (approximately 30 minutes); second, mixing 80.00 grams of aloe vera juice with 8.00 grams of xanthan gum until there are no clumps of xanthan gum present (the mixture should preferably be allowed to thicken for one to two hours); third, mixing 100.00 grams of aloe vera juice with 200.00 grams of xylitol until the xylitol is dissolved; fourth, mixing the mixtures of the first through third steps; fifth, mixing 200.00 grams of vegetable glycerin, 50.00 grams of sweet almond oil, and 4.00 grams of peppermint oil; and, sixth mixing the mixtures of the fourth and fifth steps. Those skilled in the art will appreciate how this formulation(s) may be scaled up or down to accommodate different batch sizes.

The toothpaste gel composition may also comprise: distilled water; organic whole leaf wheat grass; xylitol from Birch wood; certified organic vegetable glycerin; organic aloe vera powder; carbamide peroxide; sweet almond oil; pure peppermint oil; and xanthan gum. The disclosed composition has been preferable for ordinary oral health care when the component ingredients are featured in the following amounts: 280.00 grams of distilled water; 554.00 grams of xylitol; 4.00 grams of peppermint oil; 168.00 grams of vegetable glycerin; 0.50 grams of aloe vera powder; 100.00 grams of carbamide peroxide; 44.00 grams of sweet almond oil; 4.00 grams of wheat grass powder; and, 8.00 grams of xanthan gum.

As with the components of the rinse composition, amounts of the component ingredients within the gel composition may suitably be manipulated to adjust the oral health care properties of the composition. For instance, in another embodiment, the disclosed composition has also been preferable for treatment of sensitive oral tissue when the amount of carbamide peroxide is reduced to zero while the remaining component ingredients are featured in the following amounts: 280.00 grams of distilled water; 554.00 grams of xylitol; 4.00 grams of peppermint oil; 168.00 grams of vegetable glycerin; 0.50 grams of aloe vera powder; 44.00 grams of sweet almond oil; 4.00 grams of wheat grass powder; and, 8.00 grams of xanthan gum. In yet another embodiment, the disclosed composition has also been preferable for treatment of the oral tissue of young children (ages less than twelve years) when component ingredients plus orange oil are featured in the following amounts: 280.00 grams of distilled water; 554.00 grams of xylitol; 4.00 grams of peppermint oil; 168.00 grams of vegetable glycerin; 0.50 grams of aloe vera powder; 44.00 grams of sweet almond oil; 4.00 grams of wheat grass powder; 8.00 grams of xanthan gum; and 20.00 grams of pure orange oil. The above recited preferable compositions are summarized by Table 3.

TABLE 3

Compositions for the gel composition

| Ingredient | Amount |
| --- | --- |
| Retail Composition | |
| distilled water | 280.00 gm |
| xylitol | 554.00 gm |
| peppermint oil | 4.00 gm |
| vegetable glycerin | 168.00 gm |
| *Aloe vera* powder | 0.50 gm |
| carbamide peroxide | 100 gm |
| sweet almond oil | 44.00 gm |
| wheat grass powder | 4.00 gm |
| xanthan gum | 8.00 gm |
| Sensitive Oral Tissue Composition | |
| distilled water | 280.00 gm |
| xylitol | 554.00 gm |
| peppermint oil | 4.00 gm |
| vegetable glycerin | 168.00 gm |
| *Aloe vera* powder | 0.50 gm |
| sweet almond oil | 44.00 gm |
| wheat grass powder | 4.00 gm |
| xanthan gum | 8.00 gm |
| Gel Composition for Children | |
| distilled water | 280.00 gm |
| xylitol | 554.00 gm |
| peppermint oil | 4.00 gm |
| vegetable glycerin | 168.00 gm |
| *Aloe vera* powder | 0.50 gm |
| sweet almond oil | 44.00 gm |
| wheat grass powder | 4.00 gm |
| xanthan gum | 8.00 gm |
| orange oil | 20.00 gm |

A 1,132.00 gram batch of the toothpaste gel composition for ordinary oral health care may be prepared by: first, mixing 200.00 grams of distilled water, 100.00 grams of carbamide peroxide, and 554.00 grams of xylitol until the carbamide peroxide and xylitol are dissolved or thoroughly hydrated by the water (approximately 30 minutes); second, slowly mixing 80.00 grams of water with 8.00 grams of xanthan gum until no clumps of xanthan gum are present (the mixture should preferably be allowed to thicken for one to two hours); third, mixing 0.5 grams of aloe vera powder with 4.00 grams of wheat grass powder; fourth, mixing 168.00 grams of vegetable glycerin, 44.00 grams of sweet almond oil, 4.00 grams of peppermint oil, and the resultant mixture from the third step; fifth, mixing the mixtures from the first and fourth steps at high speed until homogenous; and sixth, mixing the mixtures from the second and fifth steps at high speed until homogenous.

A 1,032.00 gram batch of the toothpaste gel for oral health care for sensitive mouth tissue may be prepared by: first, mixing 200.00 grams of distilled water and 554.00 grams of xylitol until the xylitol is dissolved or thoroughly hydrated by the water (approximately 30 minutes); second, slowly mixing 80.00 grams of water with 8.00 grams of xanthan gum until no clumps of xanthan gum are present (the mixture should preferably be allowed to thicken for one to two hours); third, mixing 0.5 grams of aloe vera powder with 4.00 grams of wheat grass powder; fourth, mixing 168.00 grams of vegetable glycerin, 44.00 grams of sweet almond oil, 4.00 grams of peppermint oil, and the resultant mixture from the third step until no clumps of the mixture from the third step are present; fifth, mixing the mixtures from the first and fourth steps at high speed until homogenous; and sixth, mixing the mixtures from the second and fifth steps at high speed until homogenous.

A 1,052.00 gram batch of the toothpaste gel for oral health care for sensitive mouth tissue may be prepared by: first, mixing 200.00 grams of distilled water and 554.00 grams of xylitol until the xylitol is dissolved or thoroughly hydrated by the water (approximately 30 minutes); second, slowly mixing 80.00 grams of water with 8.00 grams of xanthan gum until no clumps of xanthan gum are present (the mixture should preferably be allowed to thicken for one to two hours); third, mixing 0.5 grams of aloe vera powder with 4.00 grams of wheat grass powder; fourth, mixing 168.00 grams of vegetable glycerin, 44.00 grams of sweet almond oil, 4.00 grams of peppermint oil, 20.00 grams of orange oil, and the resultant mixture from the third step until no clumps of the mixture from the third step are present; fifth, mixing the mixtures from the first and fourth steps at high speed until homogenous; and sixth, mixing the mixtures from the second and fifth steps at high speed until homogenous. Those skilled in the art will appreciate how this formulation(s) may be scaled up or down to accommodate different batch sizes.

3. The Serum

The serum may comprise: organic aloe vera juice; xanthan gum; organic whole leaf wheat grass; carbamide peroxide; sweet almond oil; pure peppermint oil; and certified organic vegetable glycerin. A first embodiment of the disclosed composition may comprise the component ingredients in the following amounts: 40.00 grams of organic aloe vera juice; 3.00 grams of xanthan gum; 4.00 grams of wheat grass powder; 26.00 grams of carbamide peroxide; 6.00 grams of sweet almond oil; 2.00 grams of peppermint oil; and 100.00 grams of vegetable glycerin. A second embodiment of the disclosed composition may comprise the component ingredients in the following amounts: 40.00 grams of aloe vera juice; 3.00 grams of xanthan gum; 4.00 grams of wheat grass powder; 26.00 grams of carbamide peroxide; 12.00 grams of sweet almond oil; 2.00 grams of peppermint oil; and 100.00 grams of vegetable glycerin. A third embodiment of the disclosed composition may comprise the component ingredients in the following amounts: 40.00 grams of aloe vera juice; 3.00 grams of xanthan gum; 4.00 grams of wheat grass powder; 13.00 grams of carbamide peroxide; 12.00 grams of sweet almond oil; 2.00 grams of peppermint oil; and 100.00 grams of vegetable glycerin. A fourth embodiment of the disclosed composition may comprise the component ingredients in the following amounts: 40.00 grams of Organic aloe vera juice; 2.00 grams of xanthan gum; 4.00 grams of wheat grass powder; 26.00 grams of carbamide peroxide; 6.00 grams of sweet almond oil; 2.00 grams of peppermint oil; and 100.00 grams of vegetable glycerin. A fifth embodiment of the disclosed composition may comprise the component ingredients in the following amounts: 40.00 grams of aloe vera juice; 2.00 grams of xanthan gum; 4.00 grams of wheat grass powder; 26.00 grams of carbamide peroxide; 12.00 grams of sweet almond oil; 2.00 grams of peppermint oil; and 100.00 grams of vegetable glycerin. A sixth embodiment of the disclosed composition may comprise the component ingredients in the following amounts: 40.00 grams of aloe vera juice; 2.00 grams of xanthan gum; 4.00 grams of wheat grass powder; 13.00 grams of carbamide peroxide; 12.00 grams of Sweet Almond Oil; 2.00 grams of peppermint oil; and 100.00 grams of vegetable glycerin. The above recited preferable compositions are summarized by Table 4.

TABLE 4

Compositions for the serum

| Ingredient | Amount |
|---|---|
| Serum #1 | |
| *Aloe vera* juice | 40.00 gm |
| xanthan gum | 3.00 gm |
| wheat grass | 4.00 gm |
| carbamide peroxide | 26.00 gm |
| sweet almond oil | 6.00 gm |
| peppermint oil | 2.00 gm |
| vegetable glycerin | 100.00 gm |
| Serum #2 | |
| *Aloe vera* juice | 40.00 gm |
| xanthan gum | 3.00 gm |
| wheat grass | 4.00 gm |
| carbamide peroxide | 26.00 gm |
| sweet almond oil | 12.00 gm |
| peppermint oil | 2.00 gm |
| vegetable glycerin | 100.00 gm |
| Serum #3 | |
| *Aloe vera* juice | 40.00 gm |
| xanthan gum | 3.00 gm |
| wheat grass | 4.00 gm |
| carbamide peroxide | 13.00 gm |
| sweet almond oil | 12.00 gm |
| peppermint oil | 2.00 gm |
| vegetable glycerin | 100.00 gm |
| Serum #4 | |
| *Aloe vera* juice | 40.00 gm |
| xanthan gum | 2.00 gm |
| wheat grass | 4.00 gm |
| carbamide peroxide | 26.00 gm |
| sweet almond oil | 6.00 gm |
| peppermint oil | 2.00 gm |
| vegetable glycerin | 100.00 gm |
| Serum #5 | |
| *Aloe vera* juice | 40.00 gm |
| xanthan gum | 2.00 gm |
| wheat grass | 4.00 gm |
| carbamide peroxide | 26.00 gm |
| sweet almond oil | 12.00 gm |
| peppermint oil | 2.00 gm |
| vegetable glycerin | 100.00 gm |

TABLE 4-continued

Compositions for the serum

| Ingredient | Amount |
|---|---|
| Serum #6 | |
| Aloe vera juice | 40.00 gm |
| xanthan gum | 2.00 gm |
| wheat grass | 4.00 gm |
| carbamide peroxide | 13.00 gm |
| sweet almond oil | 12.00 gm |
| peppermint oil | 2.00 gm |
| vegetable glycerin | 100.00 gm |

181.00 grams of the first embodiment of the serum may preferably be prepared by: first, mixing 4.00 grams of aloe vera juice with 4.00 grams of wheat grass until the wheat grass powder is thoroughly hydrated; second, slowly mixing 3.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 26.00 grams of carbamide peroxide until the carbamide peroxide is thoroughly dissolved; fourth, mixing 100.00 grams of vegetable glycerin, 6.00 grams of sweet almond oil, and 3.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

187.00 grams of the second embodiment of the serum may preferably be prepared by: first, mixing 4.00 grams of aloe vera juice with 4.00 grams of wheat grass until the wheat grass powder is thoroughly hydrated; second, slowly mixing 3.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 26.00 grams of carbamide peroxide until the carbamide peroxide is thoroughly dissolved; fourth, mixing 100.00 grams of vegetable glycerin, 12.00 grams of sweet almond oil, and 2.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

174.00 grams of the third embodiment of the serum may preferably be prepared by: first, mixing 4.00 grams of aloe vera juice with 4.00 grams of wheat grass until the wheat grass powder is thoroughly hydrated; second, slowly mixing 3.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 13.00 grams of carbamide peroxide until the carbamide peroxide is thoroughly dissolved; fourth, mixing 100.00 grams of vegetable glycerin, 12.00 grams of sweet almond oil, and 2.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

180.00 grams of the fourth embodiment of the serum may preferably be prepared by: first, mixing 4.00 grams of aloe vera juice with 4.00 grams of wheat grass until the wheat grass powder is thoroughly hydrated; second, slowly mixing 2.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 26.00 grams of carbamide peroxide until the carbamide peroxide is thoroughly dissolved; fourth, mixing 100.00 grams of vegetable glycerin, 6.00 grams of sweet almond oil, and 2.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

186.00 grams of the fifth embodiment of the serum may preferably be prepared by: first, mixing 4.00 grams of aloe vera juice with 4.00 grams of wheat grass until the wheat grass powder is thoroughly hydrated; second, slowly mixing 2.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 26.00 grams of carbamide peroxide until the carbamide peroxide is thoroughly dissolved; fourth, mixing 100.00 grams of vegetable glycerin, 12.00 grams of sweet almond oil, and 2.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

173.00 grams of the sixth embodiment of the serum may preferably be prepared by: first, mixing 4.00 grams of aloe vera juice with 4.00 grams of wheat grass until the wheat grass powder is thoroughly hydrated; second, slowly mixing 2.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 13.00 grams of carbamide peroxide until the carbamide peroxide is thoroughly dissolved; fourth, mixing 100.00 grams of vegetable glycerin, 12.00 grams of sweet almond oil, and 2.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

B. Related Methods of Use

The disclosed compositions are suitably nutrient rich and beneficial to oral health and wellness. Suitably, the disclosed composition is non-toxic and may be used to promote oral health and wellness, protect the body, and strengthen the immune system. Additionally, the disclosed compositions are nutrient rich whereby application of the composition to components of the oral cavity results in the delivery of nutrients to the oral cavity via absorption. For example, wheat grass possesses antioxidants, 13 of the 16 amino acids (including all 8 of the essential amino acids), vitamins (A, B1, B2, B3, B5, B6, B8, B12, C, E, and K), Superoxide Dismutase (SOD), P4D1, Muco-polysacharides, and Chlorophyll which are readily absorbed by the soft tissues of an oral cavity when contacted by the disclosed composition. For another example, Sweet almond oil is rich in unsaturated fat and essential fatty acids, and Omega-3, which nutrients are readily absorbable by soft tissue. For yet another example, Additionally, the disclosed composition is rejuvinative because mineral ions within the ingredients of the composition may be taken up by saliva (a combination of the water from the saliva and the carbon dioxide from breath, i.e., carbonic acids) and restored to the teeth. Said remineralization reduces tooth sensitivity and increases enamel strength. Further, ingredients, e.g., Aloe Vera Juice or powder, within the compositions possess antiseptic agents (including: lupeol, salicylic acid, urea nitrogen, cinnomonic acid, phenols, and sulfur), treat infections, help cure wounds, and inhibit the growth of fungi, Streptococcus, and Shigella, and help reduce gingivitis, plaque, and tartar build-up. Further still, the ingredients, including sweet almond oil, strengthen the immune system and possess anti-inflammatory attributes. Finally, the composition can be used to treat dry mouth (Xerostomia) because: Sweet Almond Oil provides lubricating emollients to dry tissues; Pure Peppermint Oil gives a cooling effect to dry tissues; Vegetable Glycerin has excellent moisturizing properties which aid in retaining moisture; and, Xylitol stimulates saliva glands thereby increasing saliva in the mouth.

In use, the rinse composition may be applied to the inner components of the oral cavity. More specifically, the composition may be swished in the mouth before discarding the used composition.

As an alternative use, the rinse composition may be placed in a dispenser similar to U.S. Pat. No. 4,023,712 (issued May 17, 1977) (this and other known dispensers are hereby incorporated by reference and fully set forth herein) for sprayed application to the inner components of the oral cavity. Suitably, dry mouth (Xerostomia) may be treated by spraying certain embodiments of the rinse composition into the mouth so that the affected tissue is coated, moisturized, soothed, and/or healed. The various embodiments of the composition may further: deliver nutrients to the soft tissues of the oral cavity; treat wounds; kill pathogens and halitosis causing bacteria/fungus; and, clean, strengthen and whiten the teeth.

In use, the oral care gel or toothpaste may be applied to the inner components of the oral cavity. However, a preferable manner and system of application of the compositions for oral health care vary. In a preferable manner of application, the oral care gel or tooth paste may be applied topically to the internal components of the oral cavity via a pen or brush dispenser similar to dispensers disclosed by U.S. Pat. No. 6,474,891 (issued Nov. 5, 2002) and U.S. Pat. No. 7,309,185 (issued Dec. 18, 2007) (these and other known dispensers are hereby incorporated by reference and fully set forth herein). More specifically, the toothpaste may be placed inside the reservoir of a dispensing pen or brush and thereby topically applied to the inner components of the oral cavity without brushing or rinsing. In another preferable manner of use, the gel composition may be used to treat dry mouth (Xerostomia) via the application of the composition to the affected oral tissue by either: (a) placing the composition on a finger and spreading the composition over the affected tissue; or (b) placing the gel in a tube and directing the substance from the tube to an affected area. Suitably, the applied gel composition coats, moisturizes, soothes, and/or promotes growth and healing of the affected tissue.

The composition may: deliver nutrients to the soft tissues of the oral cavity; treat wounds; kill pathogens and halitosis causing bacteria/fungus; and, clean, strengthen and whiten the teeth.

Alternatively, the toothpaste may be used in the ordinary manner of toothpaste. More specifically, the composition may be placed on the bristles of a toothbrush and thereby applied to the teeth, gums, tongue, and other soft-tissues of the oral cavity before rinsing the used oral care gel with the rinse composition. The composition may: deliver nutrients to the soft tissues of the oral cavity; treat wounds; kill harmful pathogens and halitosis causing bacteria/fungus; and, clean, strengthen and whiten the teeth.

It should be noted that the healing properties of the toothpaste are not limited to oral applications. That is to say, the toothpaste may also be used to treat cuts or scraps. More specifically, the toothpaste may be placed inside the reservoir of a dispensing pen or brush and thereby topically applied to cuts or scrapes outside of the oral cavity to assist in wound treatment.

To combat the constant growth and contamination of bacteria, periodic delivery of toxic loads, and general degradation of oral health that occur throughout a day, this application further discloses a system for facilitating good oral health. Preferably, the system comprises: an amount (e.g., four ounces (4 oz)) of the toothpaste for use as a Brushing Gel or toothpaste; a tooth brush; an amount (e.g., sixteen ounces (16 oz)) of the mouth rinse; an amount (e.g., two milliliters (2 ml)) of the oral care gel disposed within the reservoir of a dispensing pen or brush; and an amount (e.g., one ounce (1 oz)) of the rinse composition disposed within a spray dispenser. Preferable daily use of the system may consist essentially of the following steps: (1) placing approximately one-fourth of a teaspoon of the toothpaste onto the bristles of the toothbrush and, using circular motions, cleaning the teeth, gums, tongue and other soft tissues of the mouth using the gel-plus-bristles; (2) rinsing the oral cavity of the toothpaste residue by placing approximately one-fourth ounce of the mouth rinse into the oral cavity and swishing it therein for at least sixty seconds (60 sec); (3) topically applying, without brushing or rinsing, the toothpaste gel to the teeth, gums, tongue, and soft tissues of the mouth via the dispensing pen or brush; (4) spraying the mouth spray onto the inner components of the oral cavity via the spray dispenser; (5) repeating step (3) and/or (4) periodically throughout the day; and, (6) completing steps (1) and (2) at least once more.

The serum may suitably be used for antimicrobial activity against Candida albicans, Porphyromonas gingivalis, Prevotella intermedia, Fusobacterium nucleatum, Campylobacter rectus, Actinobacillus actinomycetemcomitans (re-classified as Aggregatibacter actinomycetemomitans (Aa)) and Streptococcus mutans. In one instance: (1) fresh (24 hour broth) cultures of Candida albicans, Porphyromonas gingivalis, Prevotella intermedia, Fusobacterium nucleatum, Campylobacter rectus, Aggregatibacter actinomycetemomitans (Aa) and Streptococcus mutans were individually swabbed onto blood agar plates to provide a confluent lawn of microbial growth; (2) the inoculums were allowed to absorb into their respective agar host for 5 minutes; (3) specimens of each serum composition was aseptically pipetted (5 ul) onto designated places on the plates and allowed to adsorb (or adhere, in the case of the undiluted sera) into the agar; (4) the plates were incubated, agar-side up, at 37 deg. Celsius in GasPak anaerobic jars or in % 5 CO sub. 2 for seventy two hours; the plates were examined for zones of inhibition, wherein the diameter of each zone of inhibition was between 9 and 50 millimeters (the zone of inhibition for a chlorhexidine (0.12%) control was between 10 and 40 millimeters).

The serum may also be used with root planing, routing prophylaxis, periodontal scaling, gingival curettage, core retention techniques, extractions, and operative or post operative procedures. In a preferable mode of use, the serum may be used to fight pathogens that have infected the periodontal pocket (defined as the area located four or more millimeters below the gum-line between two teeth). In said preferred mode of use, the serum may be loaded into a syringe and injected, via an irrigation needle, into the periodontal pocket. In one instance, the serum may be injected into a periodontal pocket that is 12 to 13 millimeters below the gum line. Suitably, the viscosity of the serum allows the serum to remain in the periodontal pocket without being rejected by the natural processes of the human body. In another instance, the serum may be placed on wounds (e.g., in the socket of a tooth extraction) to promote tissue growth and fight bacterial infection.

It should be noted that the above description and recited embodiments or examples are of illustrative importance only. In other words, the descriptions of the present disclosure should not be construed as limiting of the subject matter in this application. Additional modifications may become apparent to one skilled in the art after reading this disclosure.

Example 2

This example shows in vitro analysis of antimicrobial activity of wheat grass-containing solutions Aim: This study was conducted to determine if four different formulations of wheat grass-containing oral serum solutions (labeled samples A-D) have antimicrobial activity against *Candida albicans, Porphyromonas gingivalis, Prevotella intermedia, Fusobacterium nucleatum* and *Streptococcus mutans*.

Materials and Methods

Experimental Design: Blood agar (for the 3 anaerobic bacteria, 1 facultative bacterium and 1 aerobic yeast; Fisher Scientific) plates were individually swabbed with fresh 24 h broth cultures of *C. albicans, P. gingivalis, P. intermedia, F. nucleatum* and *S. mutans* to provide a confluent lawn of microbial growth. Five minutes after swabbing the plates (to allow the inoculum to absorb into the agar), the test and control specimens (see below) were aseptically pipetted (5 ul) onto designated places on the plates and allowed to adsorb (or adhere, in the case of the undiluted sera) into the agar. Assays were conducted in duplicate and undiluted and 1:5 and 1:10 dilutions of the solutions and sterile saline (negative control) were used. The plates were incubated agar-side up at 37° C. in a GasPak anaerobic jar or in 5% $CO_2$ for 72 h. Plates were examined at 72 h for zones of inhibition of growth of the microbes. The diameter of each zone was measured in mm. The zones of inhibition of each dilution sample were compared to the zones of control saline without antimicrobial components. If the zones of the solutions were the same size (or smaller) than the inhibition zones from the control saline than there was judged no inhibition of antimicrobial activity by the antimicrobial solutions. Conversely, if the zones of the solutions were larger than the inhibition zones from the control saline than there was judged significant antimicrobial activity by the solutions. It was anticipated that there will be significant inhibition of microbial growth by at least some of the antimicrobial wheat grass products.

Base Formulation:

| *Aloe vera* Juice | 40 g | 23.67 % |
|---|---|---|
| Xanthan Gum | 4 g | 2.37 % |
| Wheat Grass | 4 g | 2.37 % |
| Carbamide Peroxide | 13 g | 7.69 % |
| Sweet Almond Oil | 6 g | 3.55 % |
| Peppermint Oil | 2 g | 1.18 % |
| Vegetable Glycerin | 100 g | 59.17% |
| *Aloe vera* Powder | | |
| Total Grams | 169 g | 100.00% |

Sample A contained:

| *Aloe vera* Juice | 10 g | 21.62% |
|---|---|---|
| Xanthan Gum | 1 g | 2.16% |
| Wheat Grass | 5 g | 10.81% |
| Carbamide Peroxide | 3.25 g | 7.03% |
| Sweet Almond Oil | 1.5 g | 3.24% |
| Peppermint Oil | 0.5 g | 1.08% |
| Vegetable Glycerin | 25 g | 54.05% |
| *Aloe vera* Powder | | |
| Total Grams | 46.25 g | 100.00% |

Sample B contained:

| Aloe *vera* Juice | 10 g | 21.60% |
|---|---|---|
| Xanthan Gum | 1 g | 2.26% |
| Wheat Grass | 1 g | 2.26% |
| Carbamide Peroxide | 3.25 g | 7.34% |
| Sweet Almond Oil | 1.5 g | 3.39% |
| Peppermint Oil | 2.5 g | 5.65% |
| Vegetable Glycerin | 25 g | 56.05% |
| *Aloe vera* Powder | | |
| Total Grams | 44.25 g | 100.00% |

Sample C contained:

| *Aloe vera* Juice | 10 g | 18.10% |
|---|---|---|
| Xanthan Gum | 1 g | 1.81% |
| Wheat Grass | 1 g | 29.41% |
| Carbamide Peroxide | 16.25 g | 2.71% |
| Sweet Almond Oil | 1.5 g | 2.71% |
| Peppermint Oil | 0.5 g | 0.9% |
| Vegetable Glycerin | 25 g | 45.25% |
| *Aloe vera* Powder | | |
| Total Grams | 55.25 g | 100.00% |

Sample D contained:

| *Aloe vera* Juice | 10 g | 23.12% |
|---|---|---|
| Xanthan Gum | 1 g | 2.31% |
| Wheat Grass | 1 g | 2.31% |
| Carbamide Peroxide | 3.25 g | 7.51% |
| Sweet Almond Oil | 1.5 g | 3.47% |
| Peppermint Oil | 0.5 g | 1.16% |
| Vegetable Glycerin | 25 g | 57.8% |
| *Aloe vera* Powder | 1 g | 2.31% |
| Total Grams | 43.25 g | 100.00% |

In addition, a line method was used in which the microorganism was inoculated in a linear manner down two streak lines on each plate. The four undiluted test samples were spotted (5 ul) within 3-5 mm of the streak lines. This should allow the diffusion of the test materials through the agar to affect any susceptible bacteria in the streak lines.

Test Specimens: undiluted antimicrobial-containing wheat grass extract oral sera (samples A-D) and 1:5 and 1:10 dilutions in sterile saline. Control Specimen: sterile saline (negative control).

Results and Conclusions

The negative control plates without any microbes did not produce any microbial growth. The saline sample did not inhibit any microorganism. The undiluted sample A oral serum inhibited growth (ranging from 21-31 mm) of *P. intermedia* only. The undiluted and 1:5 and 1:10 dilutions of sample B oral serum inhibited growth (ranging from 3-30 mm) of *P. gingivalis, P. intermedia* and *F. nucleatum*. The undiluted and 1:5 and 1:10 dilutions of sample C oral serum inhibited growth (ranging from 4-50 mm) of all 5 microbes (*S. mutans, C. albicans, P. gingivalis, P. intermedia* and *F. nucleatum*). The undiluted and 1:5 and 1:10 dilutions of sample D oral serum inhibited growth (ranging from 4-34 mm) of all 5 microbes (*S. mutans, C. albicans, P. gingivalis, P. intermedia* and *F. nucleatum*). All four oral sera (A-D) inhibited the same species in the streak line method that they inhibited in the drop technique confirming these results. Oral serum sample C clearly had the strongest activity against all 5 microbes followed by sample D.

may reduce the growth of these organisms in vivo. Overall, the serum showed greater inhibition of bacteria for *P. ainaivalis* than the Chlorhexidine by 1.6 times to about 2.3 times the zone of inhibition for the undiluted lines of C.

Example 3

This study was conducted to determine if six different formulations of wheat grass-containing solutions (labeled samples CE1, C1, LE1, L1, TP-A, and TP-B) have antimicrobial activity against *Campylobacter rectus, Actinobacillus actinomycetemcomitans* (now reclassified as *Aggregatibacter actinomycetemcomitans* (Aa), *Candida albicans, Porphyromonas gingivalis, Prevotella intermedia, Fusobacterium nucleatum* and *Streptococcus mutans*.

Materials and Methods

Experimental Design: Blood agar (for the 3 anaerobic bacteria, 3 facultative bacteria and 1 aerobic yeast; Fisher Scientific) plates were individually swabbed with fresh 24 h

TABLE 5

Eleva antimicrobial analysis - II (all values in mm diameter zone of inhibition)

| Sample | Dilution or Treatment | S. mutans | C. albicans | P. gingivalis | P. intermedia | F. nucleatum |
|---|---|---|---|---|---|---|
| A | Undiluted | | | | 21/31 | |
| | 1:5 | | | | | |
| | 1:10 | | | | | |
| | Lines | | | | 25/18 | |
| B | Undiluted | | | 23/23 faint | 30/24 | 10/7 |
| | 1:5 | | | 4/4 | 4/4 | 3/3 |
| | 1:10 | | | 4/4 | 4/4 | 4/4 |
| | Lines | | | faint/faint | 26/17 | |
| C | Undiluted | 30/32 | 20/20 | 20/18 | 50/40 | 15/14 |
| | 1:5 | 12/12 | 5/5 | 4/4 | | |
| | 1:10 | 6/6 | 4/4 | | | |
| | Lines | 17/17 | 18/21 | faint/faint | 55/48 | 20/15 |
| D | Undiluted | 14/14 faint | 17/15 faint | 18/16 | 34/30 | 8/8 |
| | 1:5 | 3/3 | 3/3 | 5/5 | 4/4 faint | 4/4 |
| | 1:10 | 3/3 | 2/0 | 5/5 | | 4/4 |
| | Lines | 14/0 | faint/faint | faint/faint | 23/35 | |

*After 3 days of incubation; zone of inhibition in mm; if no value entered implies no reaction. The two numbers refer to two separate trials, so first trial zone of inhibition/second trial zone of inhibition

TABLE 6

NOWsystem antimicrobial analysis-II

| Control Sample | Dilution or Treatment | S mutans | | P gingivalis | P. intermedia | F nucleatum |
|---|---|---|---|---|---|---|
| Chlorhexidine | 3 ul of 20% | 19 | | 25 | 24 | 40 |

| Serum Sample | Dilution or Treatment | S mutans | C. albicans | P gingivalis | P. intermedia | F nucleatum |
|---|---|---|---|---|---|---|
| B | Undiluted | | | 23/23 faint | 30/24 | 10/17 |
| | Lines | | | faint/faint | 26/17 | |
| C | Undiluted | 30/32 | 20/20 | 20/18 | 50/40 | 15/14 |
| | Lines | 17/17 | 18/21 | faint/faint | 55/48 | 20/15 |
| D | Undiluted | 14/14 faint | 17/15 faint | 18/16 | 34/30 | 8/8 |
| | Lines | 14/0 | faint/faint | faint/faint | 23/35 | |

*After 3 days of incubation; zone of inhibition in mm; if no valueentered implies no reaction Conclusion: These in vitro results indicate significant inhibition of growth of the five microbes by two of the samples (oral serum samples C and D) while sample B had less significant activity against 3 of the 5 microbial species. Oral serum sample A had very little activity against these microbes with the exception of *P. intermedia*. These results suggest that the oral serum samples C and D formulations broth cultures of *C. rectus, Aggregatibacter actinomycetemcomitans* (A.a), *C. albicans, P. gingivalis, P. intermedia, F. nucleatum* and *S. mutans* to provide a confluent lawn of microbial growth. Five minutes after swabbing the plates (to allow the inoculum to absorb into the agar), the test and control specimens (see below) were aseptically pipetted (5 ul) onto designated places on the plates and allowed to adsorb (or adhere, in the case of the undiluted sera) into the agar. Assays were conducted in duplicate and undiluted and 1:5 and 1:10 dilutions of the solutions and sterile saline (negative control) and chlorhexidine (CHX) were used. The plates were incubated agar-side up at 37° C. in a GasPak anaerobic jar or in 5% $CO_2$ for 72 h. Plates were examined at 72 h for zones of inhibition of growth of the microbes. The diameter of each zone was measured in mm. The zones of inhibition of each dilution sample were compared to the zones of control saline without antimicrobial components. If the zones of the solutions were the same size (or smaller) than the inhibition zones from the control saline than there was judged no inhibition of antimicrobial activity by the antimicrobial solutions. Conversely, if the zones of the solutions were larger than the inhibition zones from the control saline than there was judged significant antimicrobial activity by the solutions. It was anticipated that there would be significant inhibition of microbial growth by at least some of the antimicrobial wheat grass products.

In addition, a line method was used in which the microorganisms were inoculated in a linear manner down two streak lines on each plate. The four undiluted test samples were spotted (5 ul) within 3-5 mm of the streak lines. This would allow the diffusion of the test materials through the agar to affect any susceptible bacteria in the streak lines.

Test Specimens: undiluted antimicrobial-containing wheat grass extracts (samples CE1, C1, LE1, and L1) and 1:5 and 1:10 dilutions in sterile saline.

Control Specimen: sterile saline (negative control) and chlorhexidine (CHX).

The base formula was:

| Base without C.P. & 3 grams Xanthan g.) | grams | % |
|---|---|---|
| *Aloe vera* Juice | 40 | 25.81% |
| Xanthan Gum | 3 | 1.94% |
| Wheat Grass | 4 | 2.58% |
| Carbamide Peroxide |  | 0.00% |
| Sweet Almond Oil | 6 | 3.87% |
| Peppermint Oil | 2 | 1.29% |
| Vegetable Glycerin | 100 | 64.52% |
| *Aloe vera* Powder |  |  |
| Total Grams | 155 | 100.00% |

Sample C1 contained:

|  | grams | % |
|---|---|---|
| *Aloe vera* Juice | 10 | 18.26% |
| Xanthan Gum | 0.5 | 0.91% |
| Wheat Grass | 1 | 1.83% |
| Carbamide Peroxide | 16.25 | 29.68% |
| Sweet Almond Oil | 1.5 | 2.74% |
| Peppermint Oil | 0.5 | 0.91% |
| Vegetable Glycerin | 25 | 45.66% |
| *Aloe vera* Powder |  |  |
| Total Grams | 54.75 | 100.00% |

Sample CE1 contained:

|  | grams | % |
|---|---|---|
| *Aloe vera* Juice | 10 | 18.78% |
| Xanthan Gum | 0.75 | 1.41% |
| Wheat Grass | 1 | 1.88% |
| Carbamide Peroxide | 13 | 24.41% |
| Sweet Almond Oil | 3 | 5.63% |
| Peppermint Oil | 0.5 | 0.94% |
| Vegetable Glycerin | 25 | 46.95% |
| *Aloe vera* Powder |  |  |
| Total Grams | 53.25 | 100.00% |

Sample L1 contained:

|  | grams | % |
|---|---|---|
| *Aloe vera* Juice | 10 | 25.81% |
| Xanthan Gum | 0.75 | 1.94% |
| Wheat Grass | 1 | 2.58% |
| Carbamide Peroxide | 0 | 0% |
| Sweet Almond Oil | 1.5 | 3.87% |
| Peppermint Oil | 0.5 | 1.29% |
| Vegetable Glycerin | 25 | 64.52% |
| *Aloe vera* Powder |  |  |
| Total Grams | 38.75 | 100.00% |

Sample LE1 contained:

|  | grams | % |
|---|---|---|
| *Aloe vera* Juice | 10 | 24.84% |
| Xanthan Gum | 0.75 | 1.86% |
| Wheat Grass | 1 | 2.48% |
| Carbamide Peroxide | 0 | 0% |
| Sweet Almond Oil | 3 | 7.45% |
| Peppermint Oil | 0.5 | 1.24% |
| Vegetable Glycerin | 25 | 62.11% |
| *Aloe vera* Powder |  |  |
| Total Grams | 40.25 | 100.00% |

Results: The saline control spots did not produce any microbial inhibition while each of the chlorhexidine control spots inhibited the microbial growth of each species. Briefly, samples CE1, C1, LE1, and L1 in general, inhibited the seven species well. In general, the 1:5 and 1:10 dilutions of the samples did not inhibit the growth well. Aa, *P. gingivalis* and *P. intermedia* was strongly affected by the CE1 sample and Aa and *P. gingivalis* was inhibited strongly by the C1 sample but less so by LE1, and L1. *F. nucleatum*, *C. albicans* and *S. mutans* were less inhibited than the other species or not at all.

Results and Conclusions

TABLE 7

| Sample | Dilution or Treatment | *S. mutans* | *C. albicans* | *P. gingivalis* | *P. intermedia* | *F. nucleatum* | A. a. | *C. rectus* |
|---|---|---|---|---|---|---|---|---|
| CE1 | Undiluted |  |  | 40 mm | 40 mm |  | 28 mm | 22 mm |
|  | 1:5 |  |  |  |  |  |  |  |

TABLE 7-continued

| Sample | Dilution or Treatment | S. mutans | C. albicans | P. gingivalis | P. intermedia | F. nucleatum | A. a. | C. rectus |
|---|---|---|---|---|---|---|---|---|
| C1 | 1:10 Lines |  |  | 40 mm | 38 mm |  | 25 mm | 20 mm |
|  | Undiluted |  |  | 32 mm | 16 mm |  | 33 mm | 19 mm |
|  | 1:5 |  |  |  |  |  |  |  |
|  | 1:10 |  |  |  |  |  |  |  |
| LE1 | Lines |  |  | 35 mm | 14 mm |  | 30 mm | 15 mm |
|  | Undiluted | 14 mm |  | 13 mm |  |  | 9 mm |  |
|  | 1:5 |  |  |  |  |  |  |  |
|  | 1:10 |  |  |  |  |  |  |  |
| L1 | Lines | 10 mm |  |  | 10 mm |  |  |  |
|  | Undiluted | 11 mm |  | 9 mm |  |  | 12 mm |  |
|  | 1:5 |  |  |  |  |  |  |  |
|  | 1:10 |  |  |  |  |  |  |  |
| CHX | Lines |  |  | 10 mm |  |  | 10 mm |  |
|  |  | 16 mm | 20 mm | 14 mm | 20 mm | 15 mm | 11 mm | 16 mm |
| Saline |  |  |  |  |  |  |  |  |

*After 5 days of incubation (no siginificant change from 2 days); circumference of zone of inhibition in mm; if no value entered implies no reaction These in vitro results indicate significant inhibition of growth of the seven microbes by five of the six samples (samples CE1, C1, LE1, and L1). These results suggest that the CE1, C1, LE1, and L1 formulations may reduce the growth of these organisms in vivo. The results showed that both CE1 and C1 inhibited more bacteria than Chlorhexidine. CE1 also inhibited more bacteria than *P. intermeida*. All serum formulations inhibited more bacteria than A.a. CE1 and C1 also inhibited more bacteria for *C. rectus* than Chlorhexidine.

Example 4

This example will illustrate the serum of the present invention removing debris from the oral cavity Materials and Methods The debris in the oral cavity of several human volunteers will be accessed. There will be one control that receives no serum and one test control that utilizes a commercial composition for removing oral debris. The rest of the volunteers will be treated with the oral serum of the present invention. The amount of oral debris will be accessed after treatment with the serum of the present invention. The amount of oral debris determined after treatment with the serum of the present invention will then be compared to the amount of the debris prior to treatment with the serum. This number will also be compared with those received the other commercial composition for removing oral debris. Analysis of the results will follow.

Results and Conclusions

The results will show that the serum of the present invention removed more debris than did the commercial composition for removing oral debris. Further, it will be found that the serum of the present invention penetrated the gum line further to remove debris from an area that the commercial composition did not reach.

Example 5

This example will illustrate the synergistic effect of the serum of the present invention.

Materials and Methods

Each component of the serum will be tested individual against several bacteria normally found in the oral cavity. A control plate will be used as well as a test control. Finally, at least one plate using the serum of the present invention will be tested against the bacteria types. The zone of inhibition of the bacteria will be measured. The results of the individual components of the serum will be compared to the zone of inhibition for the serum of the present invention.

Results and Conclusions

The results will show that the serum of the present invention inhibits a greater area of bacteria than any of the components of the serum alone. The results will support a synergistic effect between the components of the serum in their relative amounts.

The invention claimed is:

1. An oral serum for reducing bacteria comprising a vegetable glycerin, aloe vera, a nut extract or oil, wheat grass, a preservative, a binder, and menthe *piperita*, wherein the aloe vera is selected from the group consisting of aloe vera water, aloe vera juice, aloe vera powder, and combinations thereof.

2. The oral serum of claim 1, wherein the wheat grass comprises about 1% to 6% of the serum.

3. The oral serum of claim 1, wherein the preservative comprises about 0.1% to 5% of the serum.

4. The oral serum of claim 1, wherein the binder comprises about 0.8% to about 2% of the serum.

5. The oral serum of claim 1, wherein the binder is xanthan gum.

6. A toothpaste composition for reducing oral bacteria comprising a vegetable glycerin, aloe vera, a preservative, a nut extract or oil, wheat grass, a binder, menthe *piperita*, and xylitol, wherein the aloe vera is selected from the group consisting of aloe vera water, aloe vera juice, aloe vera powder, and combinations thereof.

7. The toothpaste of claim 6, wherein the xylitol is present in an amount of about 6% to 15%.

8. An oral rinse for reducing oral bacteria comprising a vegetable glycerin source, aloe vera, a preservative, a nut extract or oil, wheat grass, a binder, and menthe *piperita*, wherein the aloe vera is selected from the group consisting of aloe vera water, aloe vera juice, aloe vera powder, and combinations thereof.

9. A method for reducing disease-causing microorganisms in the oral cavity, comprising the steps of administering the composition of claim 1.

10. The method of claim 9, wherein reduction of disease-causing microorganisms is reduced by at least 10%.

11. The method of claim 9, wherein reduction of disease-causing microorganisms is reduced by at least 50%.

12. A method for increasing oral wound healing comprising administering a composition comprising a vegetable glycerin, aloe vera, a preservative, a nut extract or oil, wheat grass, a binder, and menthe *piperita*, wherein the aloe vera is selected from the group consisting of aloe vera water, aloe vera juice, and aloe vera powder combinations thereof, to an oral wound.

13. An oral serum comprising vegetable glycerin, aloe vera, a preservative, almond oil, wheat grass, xanthan gum, and peppermint oil.

14. An oral serum for reducing oral bacteria comprising 50% to 60% vegetable glycerin, 20% to 25% distilled water, 4% to 6% sweet almond oil, 1% to 3% aloe vera powder, about 1% to 3% wheatgrass powder, 1% to 2% xanthan gum, 1% to 2% peppermint oil, 0.1% to 5% preservative and 0.2% to 1% rosemary oil.

15. A toothpaste composition for reducing oral bacteria, comprising 40-50% xylitol, 10-20% vegetable glycerin, 20-30% water or aloe vera juice, 0.1% to 5% preservative, 1% to 5% almond oil, 0.5% to 2% aloe vera powder, 0.5% to 2% wheatgrass powder, 0.1% to 1% xanthan gum, 0.1% to 1% peppermint oil, 0.1% to about 1% rosemary oil, and 0.5% to about 2% arabic gum.

16. An oral rinse for reducing oral bacteria comprising 10% to about 20% xylitol, 45% to about 60% distilled water, 0.1% to 5% preservative, 1% to about 5% sweet almond oil, 0.1% to 3% aloe vera powder, 0.1% to 3% wheatgrass powder, 0.1% to 3% xanthan gum, 0.1% to 3% peppermint oil, and 0.1% to 3% rosemary oil.

17. An oral care product comprising vegetable glycerin, a liquid, a preservative, a nut extract or oil, aloe vera, wheat grass, a binder, and menthe *piperita*.

18. A method for increasing wound healing comprising administering a composition comprising a vegetable glycerin, aloe vera, a preservative, a nut extract or oil, wheat grass, a binder, and menthe *piperita*, wherein the aloe vera is selected from the group consisting of aloe vera water, aloe vera juice, and aloe vera powder combinations thereof, to an oral wound.

19. A composition comprising a vegetable glycerin, aloe vera, a nut extract or oil, wheat grass, a preservative, a binder, and menthe *piperita*, wherein the aloe vera is selected from the group consisting of aloe vera water, aloe vera juice, aloe vera powder, and combinations thereof.

* * * * *